United States Patent [19]

Hinkle

[11] Patent Number: 4,866,428
[45] Date of Patent: Sep. 12, 1989

[54] REMOTE BATTERY CELL SPECIFIC GRAVITY AND ELECTROLYTIC LEVEL MONITOR USING FLOATS AND OPTICAL COUPLERS

[75] Inventor: Jay L. Hinkle, Justice, Ill.

[73] Assignee: Illinois Tool Works, Inc., Chicago, Ill.

[21] Appl. No.: 165,624

[22] Filed: Mar. 8, 1988

[51] Int. Cl.⁴ ............................................. G08B 21/00
[52] U.S. Cl. .................................. 340/636; 340/619; 340/624; 73/293; 73/447; 73/307; 320/48
[58] Field of Search ...................... 340/636, 619, 624; 73/32 R, 447, 293, 311, 314, 306, 307, 308, 327; 324/432, 434; 116/227; 250/231 R, 222.1; 320/48

[56] References Cited

U.S. PATENT DOCUMENTS

| | | | |
|---|---|---|---|
| 3,597,973 | 8/1971 | Ryder | 73/447 |
| 3,651,471 | 3/1972 | Haselwood et al. | 455/2 |
| 3,786,343 | 1/1974 | Ehlers | 324/434 |
| 3,893,339 | 7/1975 | Melone | 73/327 |
| 3,895,235 | 7/1975 | Melone | 73/308 |
| 3,895,964 | 7/1974 | Sakamoto | 73/447 |
| 3,968,687 | 7/1976 | Fester | 73/447 |
| 3,977,908 | 8/1976 | Kitai | 73/327 |
| 4,329,406 | 5/1982 | Dahl et al. | 73/32 R |
| 4,352,067 | 9/1982 | Ottone | 324/434 |

FOREIGN PATENT DOCUMENTS

0041778 3/1985 Japan ................................ 73/32 R

Primary Examiner—Joseph A. Orsino
Assistant Examiner—Jill D. Jackson
Attorney, Agent, or Firm—Schwartz & Weinrieb

[57] ABSTRACT

A system and sensor for remotely monitoring the state of the condition of the electrolyte within each of the battery cells of a power supply is disclosed. The system includes a sensor having a dual ball-float and track arrangement for shuttering a pair of light sources and so as to independently detect and differentiate predetermined low electrolyte specific gravity and a low level of the electrolyte. Two multiplexing units receive the sensor signals and display separate indications of each battery and the states detected. The detector uses a gravity responsive ball disposed within a track that shutters one light source at a predetermined low specific gravity and a second level responsible ball within a second track located above the gravity track and ball. The level ball has a specific gravity which is less than that of the specific gravity responsive ball and shutters the second light source at a predetermined low electrolyte level independently of changes in the specific gravity of the electrolyte.

20 Claims, 4 Drawing Sheets

REMOTE BATTERY CELL SPECIFIC GRAVITY AND ELECTROLYTIC LEVEL MONITOR USING FLOATS AND OPTICAL COUPLERS

FIELD OF THE INVENTION

This invention relates to a system for remotely monitoring the state of the condition of each one of a plurality of battery cells comprising a primary or auxiliary power supply. The invention further relates to a novel sensor for monitoring and distinguishing between a low electrolyte level and a low electrolyte specific gravity.

BACKGROUND OF THE INVENTION

In certain primary or auxiliary electrical power supplies, a group of batteries, such as lead acid batteries, are connected together in a string so as to provide power back-up, load management or an uninterruptable power supply. Such a system is used in, for example, typical telephone and communication applications. In these applications, 48 volts are required and is achieved by stringing 24, 2-volt, single-cell batteries together. Typically, multiple strings of from 6 to 12 strings of battery cells are often connected to the power supply in parallel. It can be seen that such a power supply system can include from 24 up to 144 separate battery cells. Each battery cell must be monitored either periodically or more preferably continually for its state of condition. It is also preferable that the condition of each battery be remotely indicated Heretofore, individual cell and battery strings have been either locally or remotely monitored for cell terminal voltage. However, due to the requirement that the cells remain connected to the load at all times, and also due to associated charging systems, the cell terminal voltage has been recorded with the batteries still connected with the result that inaccurate terminal voltages are read.

Another and preferable means for determining the state of the condition of the individual cells is to obtain specific gravity readings of the electrolyte of each cell which has heretofore been done manually. Manual measurement and recordation of specific gravity is very time consuming, laborious, and also only provides an instantaneous indication of the cell's condition. Information is not known about the cell's condition during periods between readings and adverse conditions will not be detected at all if the condition returns to normal between readings. Also, electrolyte level has been individually, manually or visually checked which is also very time consuming, costly and does not give a continuous indication of the state of the electrolyte level.

Visual hydrometers and indicators do exist as does at least one combination visual, electronic remote indicating device. That device is disclosed in U.S. Pat. No. 3,954,010. Strictly visually indicating devices have two principal shortcomings. First, because they operate strictly in connection with visual observances, remote signaling is not possible and accordingly an observer must visually check each individual indicator at each battery cell in the string which is very labor intensive and time consuming. Furthermore, it is well known that indicators that work strictly in accordance with visual techniques cannot distinguish the difference between a low electrolyte level condition and both low specific gravity and low electrolyte level conditions occurring at the same time.

The remote indicating device of U.S. Patent 3,954,010 also suffers from significant shortcomings. First, although the device sends an electrical signal to a remote location, the meaning of the signal is not known. That is, the electronic signal can be due to either a low electrolyte level condition, or a low electrolyte specific gravity condition or both conditions occurring simultaneously.

Accordingly, the device does not electronically differentiate between such conditions or indicate which condition is occurring or if both conditions are occurring. The observer must then physically view the visual indicator portion of the device which defeats the remote signal objective and, as noted, the visual indicator portion does not distinguish the difference between a low electrolyte level and both low specific gravity and low electrolyte level conditions occurring simultaneously.

OBJECTS OF THE INVENTION

It is therefore an object of the present invention to provide for a system for monitoring the individual states of condition of the electrolyte in each battery cell in the string of batteries forming a power system.

Another important object of the invention is to provide for a system that provides a remote indication of the condition of the electrolyte within each cell.

Another object of the invention is to provide for a system which differentiates between the state of the electrolyte level and the state of the specific gravity of the electrolyte for each battery cell within the system.

SUMMARY OF THE INVENTION

According to the invention, there is provided a novel sensor mountable within each battery cell of the system which monitors, differentiates, and generates independent electrical signals representing a predetermined low electrolyte level and a predetermined low specific gravity level.

According to the invention, the system includes circuit means for the low electrolyte level and low specific gravity signals and for providing indications as to which battery cell or cells is experiencing either, or both, a low electrolyte level and a low specific gravity condition. According to an important feature of the invention, the circuit means includes at least two multiplexing units for receiving the low electrolytes level signals and for receiving the low specific gravity signals.

According to yet another important aspect of the invention, each multiplexing unit is adapted to provide a signal indication as to the specific battery cell experiencing a low electrolyte level or low specific gravity condition.

A still further important feature of the invention provides for each multiplexing unit to be adapted to provide an output signal to a telephone system remote access system for monitoring at a central office.

According to the invention, the sensor includes means for simultaneously, independently sensing and differentiating between a low electrolyte level and a low specific gravity of the electrolyte.

According to another important aspect of the invention, separate differentiated electrical signals representing the low electrolyte level and low specific gravity conditions are generated and are then displayed in the form of an alarm by appropriate external electrical circuit means.

According to yet another important feature, the means for detecting and differentiating the aforementioned conditions includes a dual ball and track sensor arrangement wherein a specific gravity responsive ball is disposed within a lower track which has a specific gravity whereby the ball assumes a predetermined position within the track at a predetermined low electrolyte specific gravity. The ball interrupts a light beam so as to cause a signal representative of the low specific gravity to be generated.

Another feature of the invention provides for a second ball disposed within a second, upper track located above the lower track and which has a specific gravity less than that of the specific gravity responsive first ball. Preferably the upper, level responsive, ball has a specific gravity such that the ball always floats upon top of the electrolyte even when in a discharged state.

Advantageously, the upper ball accordingly is only responsive to changes in electrolyte level and assumes a predetermined position within the upper track at a predetermined low electrolyte level.

A still further important feature provides for the upper, level responsive, ball to interrupt a second light beam and effect a signal representing the low electrolyte level state. Since each ball responds respectively only to changes in specific gravity and electrolyte level the two conditions are differentiated from each other.

A still further important feature of the invention provides for the sensor detector to be mounted within a probe whose axial length is adjustable. Accordingly, the sensor is adjustable for use within battery cells of different depths.

Another feature provides for a printed circuit board to be mounted inside of the probe and includes circuitry for electrically coupling the light sources and the light detectors to the external circuitry.

BRIEF DESCRIPTION OF THE DRAWINGS

The invention will be better understood after reading the following Detailed Description Of The Preferred Embodiment in conjunction with the drawings in which:

FIGS. 4A, 4B, 4C, 4D are side views of the ball and track detector taken in the direction of arrow A in FIG. 2 shown in various states of operation wherein, FIG. 4A shows the location of the detector balls when both the level and specific gravity of the electrolyte are at their proper levels, FIG. 4B shows the location of the detector balls when the electrolyte is at the proper level and the electrolyte specific gravity is below a predetermined low level, FIG. 4C shows the location of the detector balls when the electrolyte specific gravity is proper but the electrolyte level is below a predetermined low level and FIG. 4D shows the location of the detector balls when both the level and specific gravity of the electrolyte are below their predetermined low levels.

DETAILED DESCRIPTION OF THE PREFERRED EMBODIMENT

Figure 1:
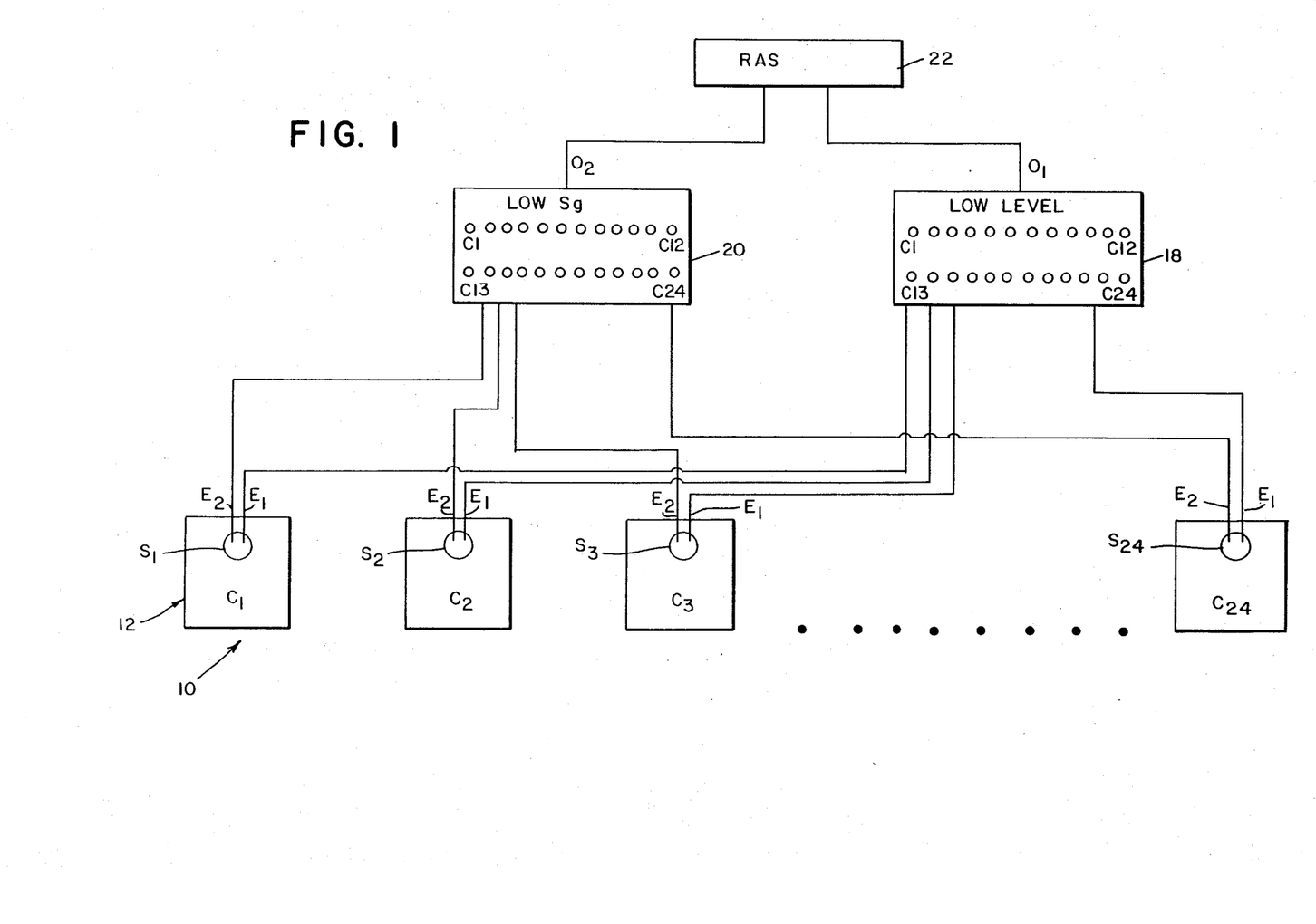
FIG. 1 is a block diagram of a system according to the invention for remotely monitoring the state of the condition of the electrolyte within the individual battery cells within a telephone power system.

Shown in FIG. 1 is a block diagram of a telephone system power supply 10 including a string of 2 volt batteries C1, C2, C3 . . . C24. The batteries are connected so as to yield a 48 volt supply of electrical power to a telephone circuit, not shown. It is to be understood that the system described herein for monitoring the state of the condition of the electrolyte disposed within each battery cell is not limited to a 24 cell system but rather may be used with a single cell or any number of cells, less than, equal to or greater than 24. For example, it is contemplated that one system would monitor one string of batteries consisting of 24 cells and that typically from 6 to 12 strings of batteries are connected in parallel. Accordingly, typically, 6 to 12 monitoring systems would be required to monitor the individual strings of cells.

Figure 3:
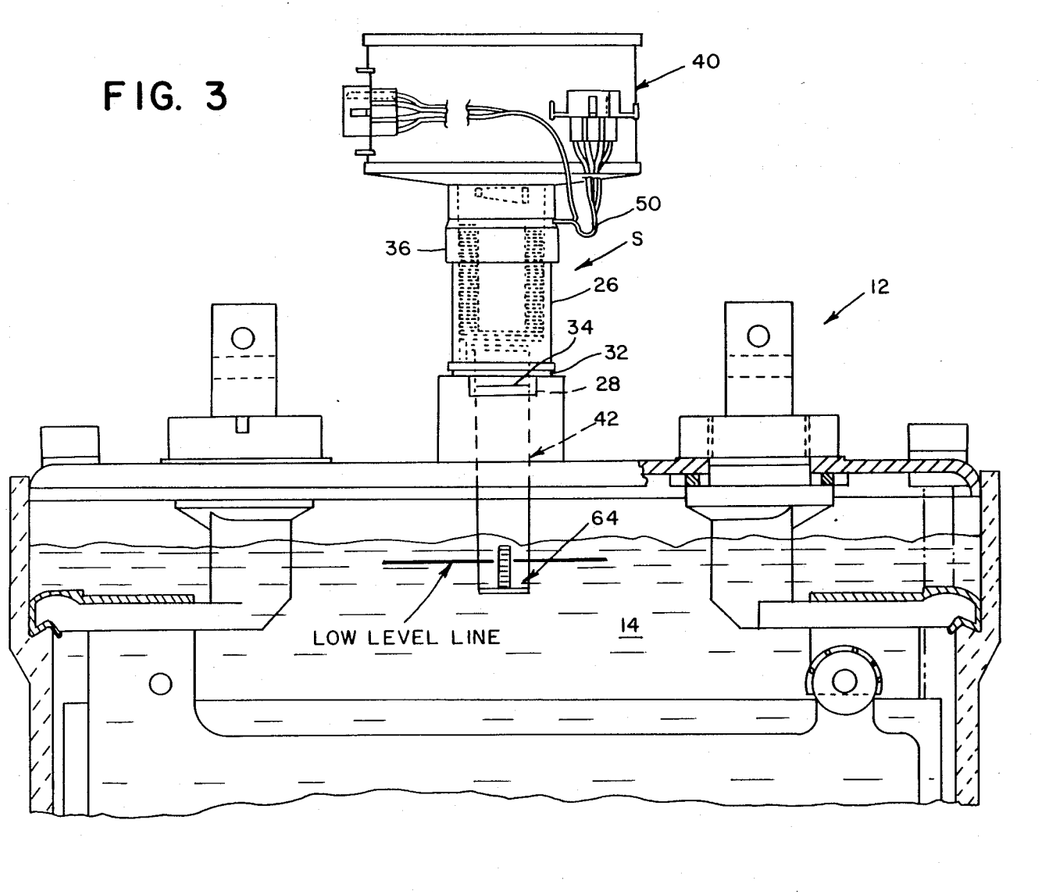
FIG. 3 is a partial side view of a battery cell with a portion cut away showing the details of the mounting of the sensor according to the invention as mounted within the battery cell.

The battery cell used within such power systems is a 2 volt lead acid battery 12 as shown in FIG. 3 having a liquid electrolyte 14. The condition of each battery cell depends upon two principal factors: the specific gravity of the electrolyte and the level of the electrolyte within the cell. The system according to the invention uses a novel sensor S1, S2 . . . S24, described within detail below, in each battery to detect, differentiate between and generate individual electrical signals representing a state of predetermined low electrolyte specific gravity and/or low electrolyte level within each cell. One sensor is used for monitoring each cell and each sensor accordingly generates two independent electrical signals E1, E2.

Each sensor is electrically coupled to two separate multiplexing units 18, 20. One output, E1, from each sensor representing a low electrolyte level is input to the level multiplexing unit 18 and the output E2 from each sensor is input into the low specific gravity multiplexing unit 20. Each multiplexing unit includes circuitry for displaying a visual or audible alarm for indicating which battery cell or cells is experiencing a low electrolyte level and/or low specific gravity condition. Also, each multiplexing unit is adapted to generate binary outputs 01, 02 for input into an existing remote access system (RAS) computer 22 of the telephone or communication system. The construction of the circuitry of each multiplexing unit required for receiving the plurality of input signals and displaying the output signals is well within the skill of one skilled in electronics having the benefit of this disclosure and is not disclosed in detail here.

As noted, FIG. 3 shows a typical lead acid battery cell 12 having an electrolyte 14. The electrolyte within a lead acid battery has a known predetermined range of specific gravity values providing for proper voltage and current output from the cell. Below a known predetermined specific gravity valve or level the state of charge and condition of the cell becomes unsatisfactory. It is also generally accepted that the specific gravity of the electrolyte of a fully discharged lead acid battery is approximately 1.104.

Furthermore, every battery cell has a range of acceptable levels of electrolyte within the cell. Below a known predetermined level performance and life of the battery is adversely affected. Further, the sizes, shapes and thus the depths of different cells vary causing the acceptable level of electrolyte to vary between different battery cell configurations. The sensor according to the invention accommodates cells of different depths.

Figure 2:
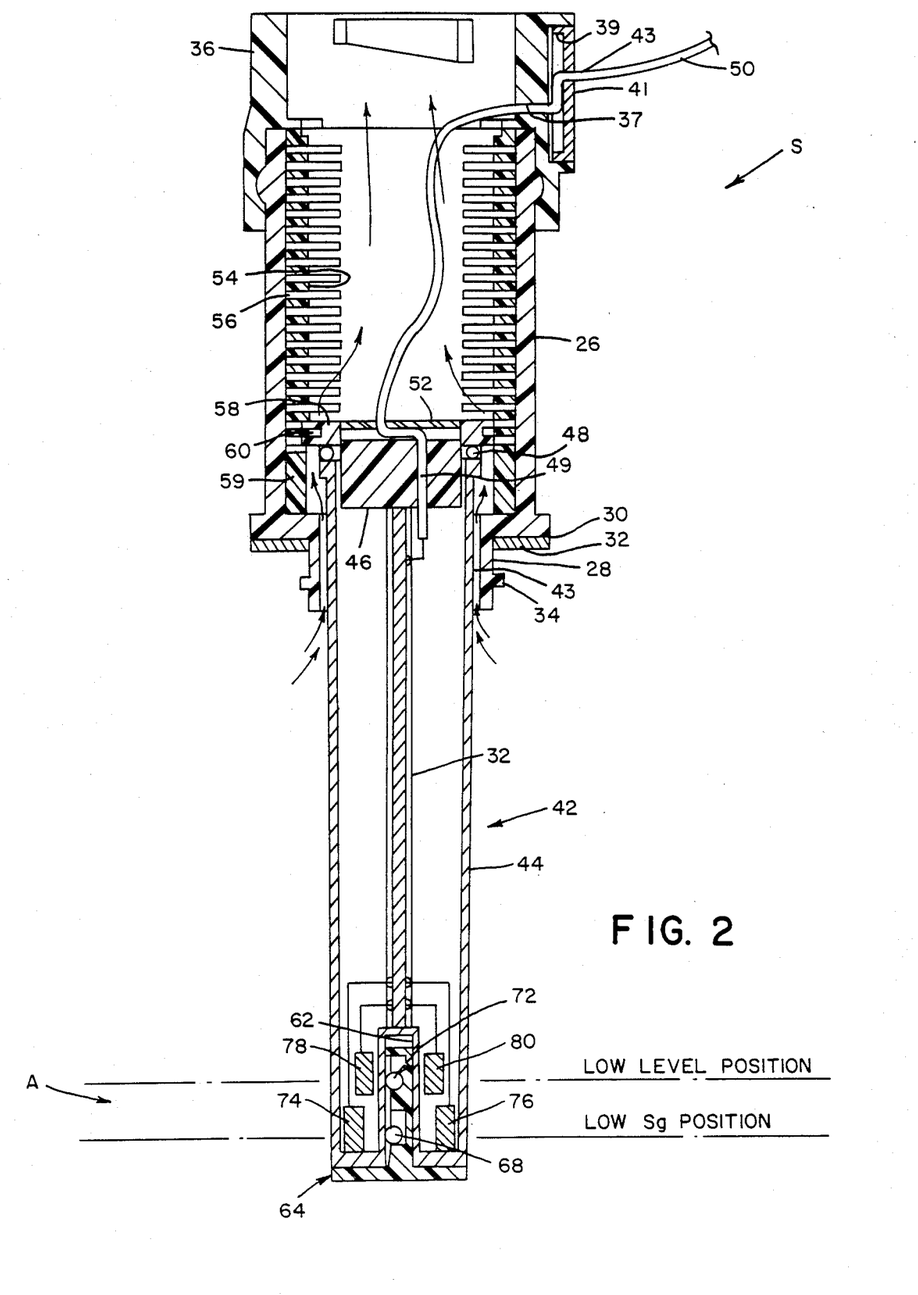
FIG. 2 is a longitudinal cross sectional view of a preferred embodiment of a sensor according to the invention showing the details of the construction thereof.

Shown in FIG. 2 is a cross section of a sensor S used within the system. The sensor includes a tubular body 26 which is open at one of its oppositely disposed ends. One end of the body has a reduced diametrical noselike portion 28 and a flat shoulder 30 for receiving a gasket 32. The nose is configured so as to be received within an opening defined within the battery cell with the gasketed shoulder disposed against the top of the battery. The nose 28 is provided with a pair of diametrically opposite flanges or alternatively a thread configuration 34 to be received within threads provided in the opening of the battery cell. The nose is mounted within the battery cell opening as shown in FIG. 3 by removing a normal battery cell cap and replacing the same with a sensor of the present invention, the nose threads or flanges 34 being threadedly engaged with the threads within the opening. When installed, the sensor is orientated vertically as shown in FIG. 3.

The opposite end of the body 26 is provided with a cylindrical cap 36 having a standard one-quarter turn attachment member on its inner surface for receiving a standard flame arrestor 40 as shown in FIG. 3. Preferably, the cap 36 is sealed to the body 26 with a sealant. The cap 36 is provided with an aperture 37 and a recess 39 in its sidewall through which an electrical cable 50 passes from the interior of the body. A sealing plug or disc 41 is sealed within the recess 39 and the cable 50 is bent in an L-shaped configuration as the same passes through the recess 39 and out an aperture 43 defined within the disc 41 thereby providing strain relief for cable 50. With the flame arrestor attached, the cavity inside the hollow body 26 is sealed from external contamination.

The sensor is provided with an elongated probe 42 including a tubular housing 44 closed on one end by means of a collar 46. The collar seals the one upper end through means of an o-ring 48 and is provided with an access hole 49 through which the electrical cable 50 extends from the body cavity into the cavity defined within the hollow probe. Another sealing disc 52 is sealingly disposed over the access hole 49 within a recess provided within the collar 46. The cable 50 is bent where it exits from the access hole 49, as shown in FIG. 2, providing additional strain relief therefor. A clearance space 43 is provided between the probe 42 and the inner surface of the nose 38 thereby providing a vent path for gases generated within the battery cell. Gases thus pass through the space 43, the hollow body 26 and into the flame arrester 40 as indicated by means of the arrows in FIG. 2.

The inner surface of the body 26 is provided with a plurality of axially spaced, radially inwardly extending flexible fins 54 defining radial recesses 56 between adjacent fins along substantially the entire longitudinal length of the body 26. The fins may be provided directly upon the inner surface of the body or upon a separate sleeve 59 provided inside the body. The collar 46 is provided with an annular flange 58 having an annular, radially outwardly facing groove 60 which is sized to receive the fins 54. The position of the probe 42 is accordingly adjustable and releasably retained at different axial positions along the length of the sensor by alternatively pushing or pulling the probe housing 44 so as to deflect the fins 54 serially into and out of the groove 60, thereby releasably retaining the probe at a fully retracted, fully extended or at any one of a plurality of intermediate positions therebetween relative to the mounting shoulder 30. The free-end of the probe 42 contains low electrolyte and low specific gravity detector means, and thus a gravity and level detector arrangement 64 which are located proximate the free-end of the probe, are accordingly axially adjustable relative to the body. Accordingly, the detector 64 can be positioned at different depths within different battery cell configurations.

Figures 4A, 4B, 4C, 4D:
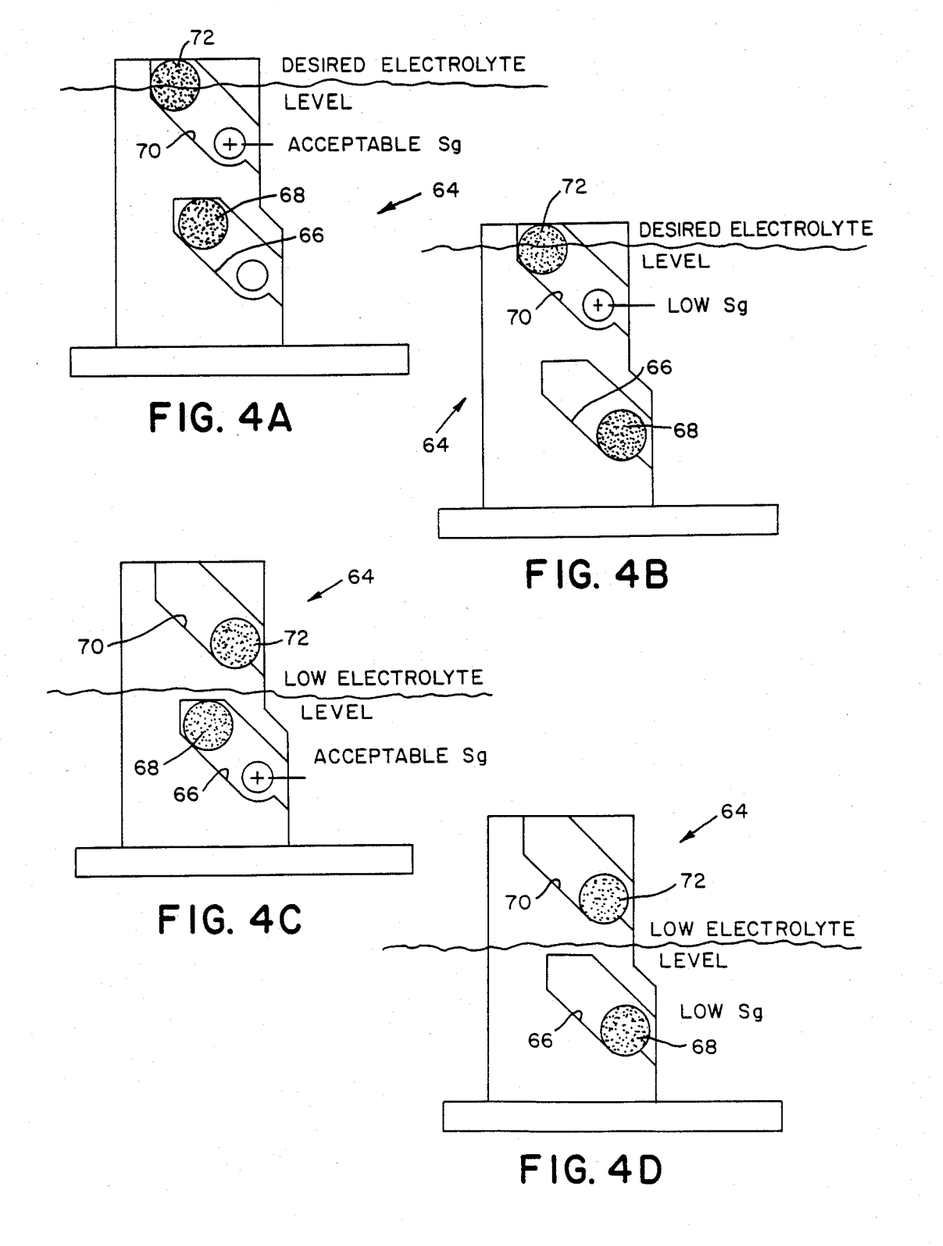

Referring to FIG. 2, the free-end of the probe housing 44 is provided with a central longitudinal slit-like relief 62. A dual ball and track detector arrangement 64 is mounted within the slit and is accordingly exposed for immersion within the electrolyte when the sensor is mounted in the battery cell opening. As shown in FIGS. 2 and 4A, B, C, D, the ball and track arrangement 64 is a generally T-shaped member with the dual track portion disposed within one leg of the T which is positioned within the slit of the probe housing. One track 66, the lower track when in the installed position, carries a specific gravity responsive ball-float 68. The ball-float 68 is received within the track 66 for movement along the track between its extreme ends. The upper track 70 is disposed above the lower track when in the installed position and carries a level responsive ball-float 72 which is received within the upper track 70 for movement between the extreme positions of that track. As shown, both tracks 66, 70 are preferably orientated at an angle to the longitudinal axis of the probe. As best shown in FIG. 2, two parallel aligned light sources and light detectors 74, 76 and 78, 80 are mounted upon opposite sides of the tracks. One pair is mounted opposite the respective lowermost positions of the balls within the tracks in the installed vertical position of the sensor.

As described below, the lowermost position of the lower ball 68 coincides with a predetermined low specific gravity level of the electrolyte and the lowermost position of the upper ball 72 coincides with a predetermined low level of electrolyte within the cell.

Mounted within the hollow probe housing 44 is a printed circuit board 82 to which the cable 50 and respective light sources and detectors are soldered. The board 82 and cable 50 accordingly couple the sources and detectors to the external circuitry.

It can be seen that the balls act as shutters by interrupting the light paths when positioned at the lowermost positions causing a signal interruption that is detected by means of the external circuitry. Accordingly, separate low electrolyte specific gravity and/or low electrolyte level signals are created at these positions. The detector arrangement provides for differentiating between a low electrolye level and a low electrolyte specific gravity. In the discussion to follow it is to be understood that all specific gravity values are relative to water. The lower, gravity, ball 68 is made with a specific gravity such that it is buoyant within an electrolyte that is in its fully charged state. The specific gravity of the lower ball is infact a value such that as the specific gravity of the electrolyte drops, the ball will begin to sink and will assume the lowermost position within the track 66 between the light source 74 and detector 76 when the specific gravity of the electrolyte reaches a predetermined low level. For a lead acid battery, the specific gravity of the gravity ball 68 preferably falls within the range of approximately 1.185 to 1.300.

The upper level responsive, ball 72 is made to have a specific gravity which is less than that of the lower ball 68 and such that it floats upon or is buoyant, within water. Preferably, the upper ball 72 has a specific gravity such that it will float upon the electrolyte of a fully discharged battery which is recognized as having a specific gravity of 1.104. It can been seen that when the upper ball 72 is less dense than the lower, gravity, ball 68, it will sink at a lower rate than the lower ball as the specific gravity of the electrolyte drops. Accordingly, the lower ball will reach the predetermined low position within the track 66 before the upper ball reaches its lowermost position within the track 70 and, therefore, only the lower ball will cause a shuttering of the sensor 74 and detector 76 upon a drop in specific gravity to its predetermined low level. Preferably, the upper ball is made so as to always float upon the electrolyte even when discharged. When that is the case, the upper ball 72 will drop in the vertical direction due solely to a physical lowering of the electrolyte level and independently of any change in the specific gravity of the electrolyte. Accordingly, the specific gravity of the upper ball 72 is within the range of approximately 0.001 and 1.180 and preferably is 1.104.

Operation of the detector as depicted in FIGS. 4A, B, C, and D is as follows: The axial position of the probe is first adjusted relative to the mounting shoulder 30 so as to place the detector arrangement at the proper depth within the particular battery cell of the system which places the lowermost position of the upper track at the predetermined electrolyte low level within the cell. The sensors are then installed within each battery of the system and electrically coupled to the multiplexing units 18, 20.

Referring to FIG. 4A, both the specific gravity and level of the electrolyte within the cell are at their proper levels and both balls assume positions disposed away from the detectors and are therefore within their uppermost positions within their respective tracks. In FIG. 4B the level of the electrolyte within the cell is at or above its correct level but the specific gravity of the electrolyte has fallen below its predetermined low level. In this situation, the upper ball remains at its uppermost position within its track while the lower, gravity, ball sinks, due to the drop of the specific gravity of the electrolyte, to its predetermined lowermost position. The lower ball thus interrupts the light beam from the light source causing a signal to be detected by means of the electronics. The low specific gravity signal corresponding to the affected cell is then generated. In FIG. 4C the specific gravity of the electrolyte is at or above its proper level but the level of the electrolyte within the cell has dropped below its predetermined low level causing the level ball to drop within its track to the predetermined low position thereby interrupting the light beam from the upper light source causing a low level signal to be detected. In FIG. 4D both the specific gravity and the level of the electrolyte have dropped below their predetermined low levels. Both balls accordingly fall and shutter the respective light beams causing both a low specific gravity signal and a low level signal to be generated and detected.

It should be noted that the sensor according to the invention does not just detect a drop of the respective floats, but distinguishes between a low specific gravity condition and a low electrolyte level condition. As noted, the external electronics are adapted to receive the multiple signals from a plurality of sensors and display the corresponding electrolyte condition in terms of low specific gravity and/or low electrolyte level and which battery cell is experiencing the condition.

Having described the Preferred Embodiment Of The Invention those skilled in the art having the benefit of such description can readily devise other embodiments and modifications. Therefore, such other embodiments and modifications are to be considered to be within the scope of the appended claims.

What is claimed is:

1. A system for remotely monitoring the state of the condition of the electrolyte within each one of a plurality of batteries defining a power source, comprising:

a plurality of sensor means, one sensor means being associated with each battery of said plurality of batteries, for simultaneously and independently sensing and differentiating between a predetermined low level of said electrolyte within each one of said batteries and a predetermined low specific gravity value of said electrolyte disposed within each one of said batteries, and for independently generating a first electrical signal responsive to said predetermined low specific gravity value of said electrolyte disposed within each one of said batteries, and a second electrical signal responsive to said predetermined low level of said electrolyte disposed within each one of said batteries, wherein each one of said plurality of sensor means includes:

(a) probe means mounted upon said associated battery and having a portion thereof immersed within said electrolyte of said associated battery;

(b) a first ball track defined within said portion of said probe means immersed within said electrolyte of said associated battery;

(c) a first ball disposed within said first ball track and having a predetermined specific gravity value such that said first ball will be disposed at a predetermined position within said first ball track when the specific gravity of said electrolyte disposed within said associated battery achieves a predetermined low specific gravity value;

(d) a second ball track defined within said portion of said probe means immersed within said electrolyte of said associated battery and disposed above said first ball track;

(e) a second ball disposed within said second ball track and having a predetermined specific gravity value which is less than that of said first ball such that said second ball is substantially independent of said specific gravity value of said electrolye disposed within said associated battery and is responsive to the level of said electrolyte disposed within said associated battery so as to be disposed at a predetermined position within said second ball track when the level of said electrolyte disposed within said associated battery achieves a predetermined low level;

(f) a first light source, for generating a first light beam, and a first light detector, for receiving said first light beam, disposed upon opposite sides of said first ball track at said predetermined position defining said low specific gravity value of said electrolyte disposed within said associated battery so as to generate said first electrical signal, indicative of said low specific gravity value of said electrolyte disposed within said associated battery, when said first ball is disposed at said predetermined position within said first ball track and is therefore interposed between said light source and said first light detector so as to block transmission of said first light beam from said first light source to said first light detector; and (g) a second light source, for generating a second light beam, and a second light detector, for receiving said second light beam, disposed upon opposite sides of said second ball track at said predetermined position defining said low electrolyte level within said associated battery so as to generate said second electrical signal, indicative of said low electrolyte level within said associated battery, when said second ball is disposed at said predetermined position within said second ball track and is therefore interposed between said second light source and said second light detector so as to block transmission of said second light beam from said second light source to said second light detector; and electrical circuit means coupled to each one of said plurality of sensor means for receiving said first electrical signal and said second electrical signal from each one of said plurality of sensor means, for generating separate low electrolyte level and low specific gravity value alarm signals in response to each one of said first electrical signals and said second electrical signals, and for indicating which one of said plurality of batteries is associated with said first and second electrical signals received.

2. The system as defined in claim 1 wherein said circuit means includes a first multiplex unit coupled to said sensor means and adapted to receive said first electrical signals from each one of said sensor means and to generate said low electrolyte level alarm signals and a second multiplex unit coupled to said sensors and adapted to receive said second electrical signals from each one of said sensor means and to and generate said low specific gravity alarm signals.

3. The system as defined in claim 2 wherein said first multiplex unit includes a first alarm output electrically coupled to a remote access system of a telephone system and said second multiplex unit includes a second alarm output electrically coupled to said remote access system of said telephone system.

4. A sensor for sensing the state of the condition of an electrolyte disposed within a battery cell, comprising:
a body having opposite ends wherein one end of said body is adapted to be mounted upon said battery within a opening leading into said battery cell;
a substantially elongated probe mounted coaxially with respect to said body and extending from said one end, and including means mounted proximate to a free end of said probe for simultaneously, independently detecting and differentiating between a predetermined low level of said electrolyte and a predetermined low specific gravity value of said electrolyte disposed within said battery cell; and
means for adjusting the axial position of said detecting and differentiating means relative to said one end of said body between a fully retracted position and a fully extended position.

5. The sensor as defined in claim 4 wherein said means for adjusting the axial position of said means for detecting includes means for adjusting the axial position of said probe relative to said body.

6. The sensor as defined in claim 5 wherein said body is substantially hollow having an opening in said one end, said probe being axially, slidably mounted in said opening between said fully retracted position and said fully extended position and means for releasably retaining said probe at said fully retracted position, at said fully extended position and at a plurality of intermediate positions between said fully retracted position and said fully extended position.

7. The sensor as defined in claim 6 wherein said means for releasably retaining said probe includes a plurality of axially spaced apart substantially diametrically opposed radially inwardly extending flexible fins on an inner wall of said body and a substantially annular radially outwardly facing groove on an outer surface of said probe proximate an end of said probe opposite said free end, said fins serially receivable in said groove and adapted to axially deflect and disengage from said groove upon application of an axial force to said probe.

8. The sensor as defined in claim 7 including an adjustment sleeve disposed within said body said adjustment sleeve includes said flexible fins.

9. The sensor as defined in claim 8 wherein said probe is tubular and closed at said free end by said means for detecting and differentiating and closed at said end opposite said free end by a collar, said collar including said groove.

10. The sensor as defined in claim 9 wherein said first track and said second track are inclined to the longitudinal axis of said probe.

11. The sensor as defined in claim 9 wherein said means for detecting and differentiating includes ball and track means mounted upon said probe for submersion in said electrolyte in an installed position of said sensor including a first track, a first ball mounted for movement in said first track said first ball having a predetermined specific gravity so as to have a predetermined buoyancy in said electrolyte at a predetermined specific gravity of said electrolyte, a second track located at a higher axial position than said first track in said installed position, a second ball mounted for movement in said second track, said second ball having a predetermined specific gravity less than the specific gravity of said first ball and two pair of aligned light sources and light detectors one pair mounted on opposite sides of said first track at a predetermined axial position, the second pair mounted on opposite sides of said second track at a predetermined axial position, whereby each one of said balls makes and breaks the light path between said respective light sources and detectors as a function of changes in specific gravity and level of said electrolyte.

12. The sensor as defined in claim 11 wherein the specific gravity of said first ball is in the range of about 1.185 to 1.300 and the specific gravity of said second ball is in the range of about 0.001 and 1.180.

13. A sensor for sensing the state of the condition of an electrolyte within a battery cell, comprising:
probe means mounted upon said battery cell and having a portion thereof immersed within said electrolyte of said battery cell;
a first ball track defined within said portion of said probe means immersed within said electrolyte of said battery cell;
a first ball disposed within said first ball track and having a predetermined specific gravity value such that said first ball will be disposed at a predetermined position within said first ball track when the specific gravity of said electrolyte achieves a predetermined low specific gravity value;

a second ball track defined within said portion of said probe means immersed within said electrolyte of said battery cell and disposed above said first ball track;

a second ball disposed within said second ball track and having a predetermined specific gravity value which is less than that of a said first ball such that said second ball is substantially independent of said specific gravity value of said electrolyte disposed within said battery cell and is reponsive to the level of said electrolyte disposed within said battery cell so as to be disposed at a predetermined position within said second ball track when the level of said electrolyte disposed within said battery cell achieves a predetermined low level;

a first light source, for generating a first light beam, and a first light detector, for receiving said first light beam, disposed upon opposite sides of said first ball track at said predetermined position defining said low specific gravity value of said electrolyte so as to generate a first signal, indicative of said low specific gravity value of said electrolyte disposed within said battery cell, when said first ball is disposed at said predetermined position within said first ball track and is therefore interposed between said first light source and said first light detector so as to block transmission of said first light beam from said first light source to said first light detector; and a second light source, for generating a second light beam, and a second light detector, for receiving said second light beam, disposed upon opposite sides of said second ball track at said predetermined position defining said low electrolyte level within said battery cell so as to generate a second signal, indicative of said low electrolyte level within said battery cell, when said second ball is disposed at said predetermined position within said second ball track and is therefore interposed between said second light source and said second light detector so as to block transmission of said second light beam from said second light source to said second light detector.

14. A sensor as set forth in claim 13, wherein:

said probe means comprises a substantially hollow, tubular probe.

15. A sensor as set forth in claim 14, furth comprising:

means for electrically connecting said first and second light sources, and said first and second light detectors, to an external circuit.

16. The sensor as defined in claim 15, wherein:

said means for electrically connecting said first and second light sources, and said first and second light detectors, to an external circuit includes a printed circuit board mounted within said hollow probe, said first and second light sources and said first and second light detectors being mounted upon said printed circuit board.

17. A sensor as set forth in claim 13, further comprising:

a substantially hollow, tubular body including means for mounting said body within an opening defined within said battery cell; and means for mounting said probe means substantially coaxially upon said body.

18. The sensor as defined in claim 17 wherein the probe is axially adjustable relative to said body.

19. The sensor as defined in claim 18 wherein the specific gravity of said first ball is at least 1.185 and the specific gravity of said second ball is not greater than 1.180.

20. The sensor as defined in claim 19 wherein the specific gravity of said second ball is 1.104.

* * * * *